United States Patent [19]
Sidransky

[11] Patent Number: 5,908,920
[45] Date of Patent: Jun. 1, 1999

[54] CELL CYCLE REGULATORY GENE

[75] Inventor: David Sidransky, Baltimore, Md.

[73] Assignee: The Johns Hopkins University School of Medicine, Baltimore, Md.

[21] Appl. No.: 09/098,317

[22] Filed: Jun. 16, 1998

Related U.S. Application Data

[62] Division of application No. 08/439,962, May 12, 1995, Pat. No. 5,767,258.

[51] Int. Cl.[6] .......................... C07K 14/00; C07H 21/04; C07H 21/02
[52] U.S. Cl. ....................... 530/350; 530/300; 536/23.1; 536/23.4; 536/23.5
[58] Field of Search .................. 435/6, 320.1; 536/231, 536/23.4, 23.5; 530/300, 350

[56] References Cited

PUBLICATIONS

Serrano et al., "A new regulatory motif in cell–cycle control causing specific inhibition of cyclin D/CDK4", *Nature,* Dec. 16, 1993, vol. 366, pp. 704–707.

*Primary Examiner*—Nancy Degen
*Assistant Examiner*—Sean McGarry
*Attorney, Agent, or Firm*—Fish & Richardson P.C.

[57] ABSTRACT

A novel cell cycle regulatory gene called 5'ALT is disclosed. Methods for determining mutations or polymorphisms in 5'ALT or 5'ALT regulated genes in tissues are also provided. Novel 5'ALT-p16 and 5'ALT-p15 transcripts and truncated expression products are also described.

3 Claims, 3 Drawing Sheets

```
TCCCGAGGCAGTTATGTGAAATATGGCCTCGATCTTGGAGTCCGGGTGGGAGTGGGGGT
GGGGTGGGGGTGGGGGTGAAGGTGGGGGGCCGCCTCAGGGAAGGCGGGTGCGCGCC
TGCGGGGGCGAGATGGGCAGGGGGCCGTGCGTGGTCCCAGTCTGCAGTTAAGGGGCAG
GAGTGGCGCTGCTCACCTCTGGTGCCAAAGGGCGGGCTGCCAGCTCCGAGCTCGGCCCT
GGAGGCGGCGAGAACATGGTGCGCAGTTCTTGGTGACCCTTCGGCGCGCGTGC
GGCCCCGCGCGAGTGAGGGTTTCGTGTTCACATCCCGCGGCTCACGGGGAGTGGGCA
GCGCCAGGGGCGCCCGCTGTGCCCTGTGCTGATGCTACTGAGGAGCCAGCGTCTA
GGGCAGCAGCCGCTTCCTAGAAGACCAGGTAGGAAAGGCCCTCGAAAGTCCGGGGCGCA
CTTGTTTTGGTGTTTGGTGTGATTCGTAAACAGATAATTCGTCTCTAGCCCATTCTAGGA
GGAGGAGGAGATAACCGCGGTGGAGGCTTCCCATTCGGGTTACAACGACTTAGACATGTG
GTTCTCGCAGTACCATTGAACCTGGACCTCCCTTCACACAGCCCTCAATCGTGGGAAACT
GAGGCGAACAGAGCTTCTAAACCACCTCAGAAGTCAGTGAGTCCCGAATATCCTGGGTG
GGAATGACTAAGACACACACACACACACACACACACACACACAGTAGGAAATGT
```

FIG. 1A

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 780 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TCCCGAGGCA GTTATGTGAA ATATGGCCTC GATCTTGGAG GTCCGGGTGG GAGTGGGGGT      60
GGGGTGGGGG TGGGGGTGAA GGTGGGGGGC GGGCGCGCTC AGGGAAGGCG GGTGCGCGCC     120
TGCGGGGCGG AGATGGGCAG GGGGCGGTGC GTGGGTCCCA GTCTGCAGTT AAGGGGGCAG     180
GAGTGGCGCT GCTCACCTCT GGTGCCAAAG GGCGGCGCAG CGGCTGCCGA GCTCGGCCCT     240
GGAGGCGGCG AGAACATGGT GCGCAGGTTC TTGGTGACCC TCCGGATTCG GCGCGCGTGC     300
GGCCCGCCGC GAGTGAGGGT TTTCGTGGTT CACATCCCGC GGCTCACGGG GGAGTGGGCA     360
GCGCCAGGGG CGCCCGCCGC TGTGGCCCTC GTGCTGATGC TACTGAGGAG CCAGCGTCTA     420
GGGCAGCAGC CGCTTCCTAG AAGACCAGGT AGGAAAGGCC CTCGAAAAGT CCGGGGCGCA     480
CTTGTTTTGT TTGGTGTGTG ATTTCGTAAA CAGATAATTC GTCTCTAGCC CATTCTAGGA     540
GGAGGAGGAG ATAACCGCGG TGGAGGCTTC CCATTCGGGT TACAACGACT TAGACATGTG     600
GTTCTCGCAG TACCATTGAA CCTGGACCTC CCTTCACACA GCCCTCAATC GTGGGAAACT     660
GAGGCGAACA GAGCTTCTAA ACCCACCTCA GAAGTCAGTG AGTCCCGAAT ATCCTGGGTG     720
GGAATGACTA AGACACACAC ACACACACAC ACACACACAC ACACACACAG TAGGAAATGT     780
```

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
TCCCGAGGTT TCTCAGAG                                                    18
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:3:

```
CAUCAUCAUC AUGAUGUCGC ACGGUACCUG                                       30
```

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:4:

```
CUACUACUAC UAACGGGUCG GGUGAGAGUG                                       30
```

(2) INFORMATION FOR SEQ ID NO:5:

(i) SEQUENCE CHARACTERISTICS:
        (A) LENGTH: 18 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:5:

AGTGGCGCTG CTCACCTC                                                18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCCCGAGGTT TCTCAGAG                                                18

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGGTGGGAAA TTGGGTAAG                                               19

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGGTCACCAA GAACCTGC                                                18

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TCCCAGTCTG CAGTTAAGG                                               19

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

```
            (xi) SEQUENCE DESCRIPTION: SEQ ID NO:10:

GTCTAAGTCG TTGTAACCCG                                              20

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

AGTGCATCAG CACGAGGG                                                18

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

AACATGGTGC GCAGGTTC                                                18

(2) INFORMATION FOR SEQ ID NO:13:

(i) SEQUENCE CHARACTERISTICS:
            (A) LENGTH: 56 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GGATCCTAAT ACGACTCACT ATAGGGAGAC CACCATGGCG CTGCTCACCT CTGGTG     56
```

CELL CYCLE REGULATORY GENE

This is divisional of U.S. application Ser. No. 08/439,962, filed May 12, 1995, now U.S. Pat. No. 5,767,258.

BACKGROUND OF THE INVENTION

1. Field of the Invention

This invention relates to regulation of cell growth and proliferation and specifically to a novel cell cycle-related polynucleotide, 5'ALT, and novel polynucleotides encoding truncated cell cyclin inhibitors, $p16^{INK4A}$ and $p15^{INK4B}$.

2. Description of Related Art

The growth cycle of eukaryotic cells is regulated by a family of protein kinases known as the cyclin-dependent kinases ("CDKs"). The cyclins and their associated CDKs move cells through the three phases of the growth cycle (G1, S and G2, respectively) leading to division in the mitosis phase (M). The cyclin/CDK complexes whose role in cellular proliferation has been most clearly defined to date are the cyclin D/CDK enzymes, which are believed to assist in the progression of the G1 growth cycle phase. Of these enzymes, cyclin D1 is believed to be an oncogene, whose overexpression stimulates excessive cell division through the continuous production of kinase, thus contributing to the development of cancers of, for example, the breast and esophagus. Cyclin D1 is specifically bound by CDK4 as part of a multi-protein complex that also consists of a protein known as p21 and cell nuclear antigen.

Known inhibitors of such cyclin/CDK overexpression include the tumor suppressor protein p53 and the protein product of the retinoblastoma (Rb) gene. Recently, two putative inhibitors of cell cyclins, $p16^{INK4A}$ and $p15^{INK4B}$, were isolated (Serrano, et al., *Nature,* 366:704, 1993; Hannon, et al., *Nature,* 371:257, 1994, respectively).

The cyclin-CDK inhibitors $p16^{INK4A}$ (CDKN2/MTS-1) and $p15^{INK4B}$ (MTS-2) are important components of cell cycle regulation. Transition through G1 is promoted by the cyclin-dependent protein kinases CDK4 and CDK6 which phosphorylate Rb resulting in release of E2F and cell cycle progression (Hunter, T. & Pines, J. ,*Cell* 79: 573–582, 1994). In addition to more universal inhibitors (Morgan, D. O., *Nature,* 374:131–134, 1995), these kinases are strongly inhibited by both $p16^{INK4A}$ and $p15^{INK4B}$. Isolation of the genes for these negative cell cycle regulators was quickly followed by their co-localization to chromosome 9p21, within a critical region commonly deleted in many types of human cancer (Kamb, A., et al., *Science,* 264:436–440, 1994; Nobori, T., et al., *Nature,* 368:753–756, 1994). Familial and sporadic malignant melanomas have been consistently associated with cytogenetic abnormalities of chromosome 9p21 (Fountain, et al, *Proc. Natl. Acad. Sci., USA,* 89:10557, 1992; Cannon-Albright, et al., *Science,* 258:1148, 1992). Deletions of this region are also common in gliomas (Olopade, et al., *Cancer Res.,* 52:2523, 1992), lung cancers (Olopade, et al., *Cancer Res.,* 53:2410, 1993), and leukemias (Olopade, et al., *Genomics,* 14:437, 1992). Although excellent tumor suppressor gene candidates, somatic point mutations were found to be rare in many primary human tumors with hemizygous loss of 9p21 (Cairns, et al. , *Science* 245:415–416, 1994).

If the cyclins are overproduced in a cell or made at an inappropriate time, they would be expected to stimulate inappropriate cell division by keeping their partner kinases "on" when they should be turned off, a malfunction that could lead to cancer or otherwise unwanted cellular proliferation. There remains a need to identify the control signals which determine whether a cell proliferates or not.

SUMMARY OF THE INVENTION

The present invention provides novel cell cycle regulatory polynucleotides and the polypeptides they encode. The polynucleotide transcripts identified herein are a product of alternative splicing mRNA of the cyclin/CDK inhibitors, $p16^{INK4A}$ and $p15^{IN4B}$, and a novel 5' nucleotide sequence referred to herein as "5'ALT".

$p16^{INK4A}$ and $p15^{IN4B}$ localize to chromosome 9p21, which has been identified as a region having homozygous deletions in many tumors. 5'ALT is shown in the present invention to also reside on chromosome 9p21, just 5' of exon 2 of $p15^{IN4B}$, and about 30 kb upstream from $p16^{INK4A}$ (see FIG. 2).

In one embodiment, the present invention provides an isolated polynucleotide having the nucleotide sequence of SEQ ID NO:1, which includes the 5'ALT sequence found in the novel transcripts described herein, as well as an upstream region which is GT-rich and a downstream element which contains a highly polymorphic CA stretch.

In a second embodiment, the invention provides a polynucleotide having a 5'ALT polynucleotide operatively linked to exon 2 and exon 3 of $p16^{INK4A}$ and the polypeptide encoded by the polynucleotide. In yet another embodiment, the invention provides a polynucleotide having a 5'ALT polynucleotide operatively linked to exon 2 of $p15^{IN4B}$ and the polypeptide encoded by the polynucleotide.

The identification of these novel transcripts which are associated with normal growth control and regulation of cellular proliferation provides a means for the development of more accurate diagnostic, prognostic and therapeutic regimes for disorders associated with control of cell cycle progression and cell differentiation and the loss of such control.

BRIEF DESCRIPTION OF THE DRAWINGS

FIG. 1a shows the polynucleotide sequence of 5'ALT (SEQ ID NO:1). The 268 bp fragment of 5'ALT contained in the $p16^{INK4A}$ and $p15^{INK4B}$ transcripts is underlined. A putative GT promoter element (bold, double-underlined) and the primer used for the primer extension assay (bold, italics, underlined) are shown. The highly polymorphic $(CA)_n$ repeat is shown on the last line.

DETAILED DESCRIPTION OF THE INVENTION

Figure 1B:
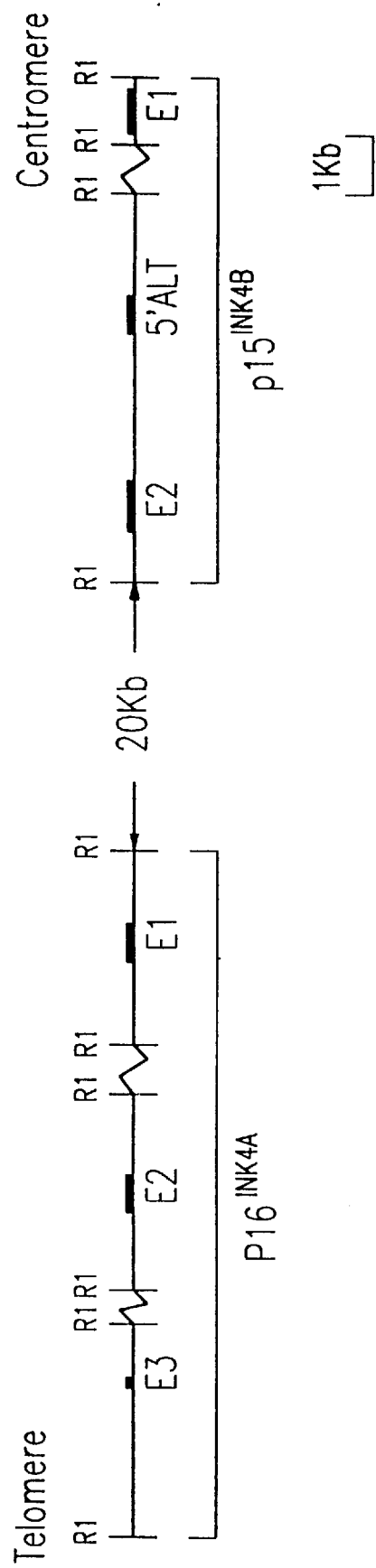
FIG. 1b shows the genomic organization of 5'ALT. Coding exons for $p15^{INK4B}$ and $p16^{INK4A}$ are designated by black boxes. E1=exon 1, E2=exon 2 and E3=exon 3. 5'ALT is located between exon 1 and 2 of $p15^{INK4B}$ and approximately 30 Kb upstreat of exon 1 of $p16^{INK4A}$.

The present invention provides novel $p16^{INK4A}$ and $p15^{INK4B}$ polynucleotides, hereafter referred to as p16 or p15, and polypeptides which are identified by a novel upstream polynucleotide sequence called "5'ALT". These novel alternative p16 and p15 transcripts generated from the novel 5'ALT sequence are involved in the complex regulation of these critical cell cycle genes.

Most nuclear messenger RNA precursors (pre-mRNA) in higher eukaryotes contain multiple introns which are precisely excised by RNA splicing. Several pre-mRNAs are alternatively spliced in different cell types or at different times during development. Alternative splicing can result in the production of more than one different protein from a single pre-mRNA. One mode of splicing can generate a mRNA that lacks an open translational reading frame, and alternative splicing of the same pre-mRNA yields a functional protein. Alternative splicing has been described in the regulatory hierarchy of sex determination of Drosophila and in many examples of tissue-specific gene expression. The novel alternative mRNAs of the invention, and the truncated proteins encoded by these transcripts, are produced as a result of alternative splicing, rather than gene rearrangement.

Initial studies in the present invention revealed that de novo methylation of a CpG island that extends into exon 1 of p16 in cell lines and primary tumors is precisely associated with transcriptional block of full length p16. Reversal of methylation with 5'-azacytidine resulted in reexpression of p16 message. However, methylated cell lines always expressed an abundant, shortened p16 transcript entirely devoid of exon 1 coding sequences (see EXAMPLE 5).

In a first embodiment, the present invention provides an isolated polynucleotide (5'ALT) having the nucleotide sequence of SEQ ID NO:1, shown in FIG. 1a, and sequences substantially complementary thereto. The invention also provides a polynucleotide having the nucleotide sequence of SEQ ID NO:1, in operative linkage with exons 2 and 3 of p16 cyclin CDK inhibitor and sequences substantially complementary thereto, as well as a polynucleotide having the nucleotide sequence of SEQ ID NO:1, in operative linkage with exon 2 of p15 cyclin CDK inhibitor and sequences substantially complementary thereto. The term "operative linkage" refers to the organization of the nucleotide sequence such that the regulatory elements and the coding sequences are in functional linkage. The term "isolated" refers to a polynucleotide substantially free of other polynucleotides, proteins, lipids, carbohydrates or other materials with which it is naturally associated.

These polynucleotides include DNA, cDNA and RNA sequences which encode either all or a portion of 5'ALT or 5'ALT in operative linkage with p16 or p15. It is understood that all polynucleotides encoding all or a portion of 5'ALT or the p16 or p15 novel transcripts are also included herein, as long as they encode a polypeptide with the corresponding activity. Such polynucleotides include naturally occurring, synthetic, and intentionally manipulated polynucleotides. For example, 5'ALT or 5'ALT-p16 or -p15 polynucleotide may be subjected to site-directed mutagenesis. The polynucleotide sequence for 5'ALT or 5'ALT-p16 or -p15 also includes complementary, or antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of 5'ALT or 5'ALT-p16 or -p15 polypeptide encoded by the nucleotide sequence is functionally unchanged.

Specifically disclosed herein is a DNA sequence containing the human 5'ALT gene. The sequence contains an open reading frame (ORF) encoding 268 base pair transcribed product. Upstream of the ORF is a GT rich region which likely contains a GT promoter element. Downstream, at the 3' end of the ORF is a highly polymorphic $(CA)_n$ stretch which can serve as a polymorphic marker. This novel 5'ALT gene was localized to chromosome 9p21 and therefore is useful as a probe for identification of this chromosomal region, which is often deleted in human cancers. As shown in the EXAMPLES, the 5'ALT-p16 product migrates at about 9–10 kD as determined by reducing SDS-PAGE. While not wanting to be bound by a particular theory, it appears that the 5'ALT-p16 expression product is translated in frame from the third methionine of p16, just inside exon 2 and a consensus Kozak sequence (consensus ribosome binding site, TGGCCATGG; Kozak, *Nucleic Acids Res.*, 15: 8125, 1987). Preferably, the human 5'ALT or 5'ALT-p16 or -p15 nucleotide sequence is the sequence of SEQ ID NO:1 including exon 2 and 3 of p16 (Serrano, et al, supra) or exon 2 of p15 (Hannon, et al., supra).

The polynucleotide encoding 5'ALT or 5'ALT-p16 or -p15 includes SEQ ID NO:1 as well as nucleic acid sequences complementary to SEQ ID NO:1 and to 5'ALT-p16 or -p15. A complementary sequence may include an antisense nucleotide. When the sequence is RNA, the deoxynucleotides A, G, C, and T of SEQ ID NO:1 is replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the truncated proteins encoded by the polynucleotides of the invention under physiological conditions. Specifically, the fragments should hybridize to DNA encoding 5'ALT or 5'ALT-p16 or -p15 protein under stringent conditions.

The present invention also includes polypeptides encoded by the 5'ALT or 5'ALT-p16 or -p15 polynucleotides of the invention. Such polypeptides are substantially pure. As used herein, the term "substantially pure" refers to a protein which is free of other proteins, lipids, carbohydrates or other materials with which it is naturally associated. One skilled in the art can purify 5'ALT or 5'ALT-p16 or -p15 polypeptides using standard techniques for protein purification. For example, the substantially pure 5'ALT-p16 polypeptide will yield a single major band of approximately 9–10 kD on a non-reducing polyacrylamide gel. The purity of the 5'ALT or 5'ALT-p16 or -p15 polypeptides can also be determined by amino-terminal amino acid sequence analysis. 5'ALT or 5'ALT-p16 or -p15 polypeptides include functional fragments of the polypeptide, as long as the activity of remains. Smaller peptides containing the biological activity of 5'ALT or 5'ALT-p16 or -p15 are included in the invention.

Minor modifications of the 5'ALT or 5'ALT-p16 or -p15 primary amino acid sequence may result in proteins which have substantially equivalent activity as compared to the 5'ALT or 5'ALT-p16 or -p15 polypeptide described herein. Such modifications may be deliberate, as by site-directed mutagenesis, or may be spontaneous. All of the polypeptides produced by these modifications are included herein as long as the biological activity of 5'ALT or 5'ALT-p16 or -p15 still exists. Further, deletion of one or more amino acids can also result in a modification ofthe structure of the resultant molecule without significantly altering its biological activity. This can lead to the development of a smaller active molecule which would have broader utility. For example, one can remove amino or carboxy terminal amino acids which are not required for 5'ALT or 5'ALT-p16 or -p15 biological activity.

The nucleotide sequence encoding the 5'ALT or 5'ALT-p16 or -p15 polypeptide of the invention includes the polypeptides encoded by the disclosed sequence (SEQ ID NO:1) in the presence or absence of exons 2 and 3 of p16, or exon 2 of p15, and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the 5'ALT or 5'ALT-p16 or -p15 polynucleotide of the invention is derived from a mammalian organism, and most preferably from human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al, *Nucl. Acid Res.,* 9:879, 1981; Maniatis, et al, *Molecular Cloning: A Laboratory Manual,* Cold Spring Harbor, N.Y. 1989).

The development of specific DNA sequences encoding 5'ALT or 5'ALT-p16 or -p15 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for 5'ALT or 5'ALT-p16 or -p15 peptides having at least one epitope, using antibodies specific for 5'ALT or 5'ALT-p16 or -p15. Such antibodies can be either polyclonally or monoclonally derived and used to detect expression product indicative of the presence of 5'ALT or 5'ALT-p16 or -p15 cDNA.

The primers used in the invention for detection or isolation of the novel 5'ALT gene, embrace oligonucleotides of sufficient length and appropriate sequence so as to provide specific initiation of polymerization on a significant number of nucleic acids in the polymorphic locus. Specifically, the term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' flanking sequences to hybridize therewith and permit amplification of the genomic locus.

Oligonucleotide primers of the invention are employed in the amplification process which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA Polymerase I (Klenow) and nucleotides, results in newly synthesized + and −strands containing the target polymorphic locus sequence. Because these newly synthesized sequences are also templates, repeated cycles of denaturing, primer annealing, and extension results in exponential production of the region (i.e., the target polymorphic locus sequence) defined by the primer. The product of the chain reaction is a discrete nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters,* 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the polymorphic locus. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from an organism found in a body sample, such as blood, urine, cerebrospinal fluid, tissue material and the like by a variety of techniques such as that described by Maniatis, et al. (*Molecular Cloning: A Laboratory Manual,* Cold Spring Harbor, N.Y., pp 280, 281, 1982). If the extracted sample is impure (such as plasma, serum, or blood), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Where the target nucleic acid sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (*Ann. Rev. Genetics,* 16:405–437, 1982).

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The amplified product may be detected by analyzing it by Southern blots without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008– 1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Preferably, the method of amplifying is by PCR, as described herein and as is commonly used by those of ordinary skill in the art. Alternative methods of amplification have been described and can also be employed as long as the 5'ALT locus amplified by PCR using the primers of the invention is similarly amplified by the alternative means. Such alternative amplification systems include self-sustained sequence replication, 3SR, which begins with a short sequence of RNA of interest and a T7 promoter. Reverse transcriptase copies the RNA into cDNA and degrades the RNA, followed by reverse transcriptase polymerizing a second strand of DNA. Another method nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$-fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair. Nucleic acid amplification by strand displacement activation (SDA) utilizes a short primer containing a recognition site for HincII with a short overhang on the 5' end which binds to target DNA. A DNA polymerase fills in the part of the primer opposite the overhang with sulfur- containing adenine analogs. HincII is added but only cut the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented temperature cycling. Although PCR is the preferred method of amplification of the invention, these other methods can also be used to amplify the 5'ALT locus as described in the present invention.

DNA sequences encoding 5'ALT or 5'ALT-p16 or -p15 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the 5'ALT or 5'ALT-p16 or -p15 polynucleotide sequences may be inserted into a recombinant expression vector. The term "recombinant expression vector" refers to a plasmid, virus or other vehicle known in the art that has been manipulated by insertion or incorporation of the 5'ALT or 5'ALT-p16 or -p15 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding 5'ALT or 5'ALT-p16 or -p15 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. Coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the 5'ALT or 5'ALT-p16 or -p$^{15}$ of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The 5'ALT or 5'ALT-p16 or -p15 polypeptides of the invention can also be used to produce antibodies which are immunoreactive or bind to epitopes of the 5'ALT or 5'ALT-p16 or -p15 polypeptides. While antibodies to p16 exon 2 and/or exon 3 or p15, exon 2, may be useful for production of antibodies, it may be desirable to utilize the truncated proteins to produce novel antibodies. While not wanting to be bound by a particular theory, the truncated protein may form additional conformational epitopes which are not present in wild-type p16 or p15 polypeptide, therefore, 5'ALT-p16 or -p15-specific antibodies are produced.

Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature*, 256:495, 1975; *Current Protocols in Molecular Biology*, Ausubel, et al., ed., 1989).

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies. A Laboratory Manual*, Cold Spring Harbor Laboratory, N.Y. (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the 5'ALT or 5'ALT-p16 or -p15 polypeptide of the invention can be prepared using an intact polypeptide or fragments containing small peptides of interest as the immunizing antigen. The polypeptide or a peptide used to immunize an animal can be derived from translated cDNA (see for example, EXAMPLE 4) or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al, Unit 9, *Current Protocols in Immunology*, Wiley Interscience, 1994, incorporated herein by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first mono-clonal antibody.

The present invention provides a method of treating a cell proliferative disorder associated with expression of 5'ALT or 5'ALT-p16 or -p15 polynucleotide(s), comprising contacting the cell having or suspected of having the disorder with a reagent which modulates 5'ALT or 5'ALT-p16 or -p15. The term "cell-proliferative disorder" denotes malignant as well as non-malignant cell populations which often appear to differ from the surrounding tissue both morphologically and genotypically. Malignant cells (i.e. cancer) develop as a result of a multistep process. Such disorders may be associated, for example, with abnormal expression of 5'ALT or 5'ALT-p16 or -p15. "Abnormal expression" encompasses increased, decreased or absent levels of expression of 5'ALT or 5'ALT-p16 or -p15, as well as expression of a mutant form of 5'ALT or 5'ALT-p16 or -p15 such that the normal function of 5'ALT or 5'ALT-p16 or -p15 is altered. Abnormal expression also includes inappropriate expression of 5'ALT or 5'ALT-p16 or -p15 during the cell cycle or in an incorrect cell type. The 5'ALT or 5'ALT-p16 or -p15 polynucleotide in the form of an antisense polynucleotide is useful in treating malignancies of the various organ systems, for example, those of epithelioid origin (e.g., lung, breast). Essentially, any disorder which is etiologically linked to altered expression of 5'ALT or 5'ALT-p16 or -p15 could be considered susceptible to treatment with a reagent of the invention which modulates mcl-1 expression. The term "modulate" envisions the suppression of expression of 5'ALTI or 5'ALT-p16 or -p15 when it is over-expressed, or augmentation of 5'ALT or 5'ALT-p16 or -p15 expression when it is under-expressed or when the 5'ALT or 5'ALT-p16 or -p15 expressed is a mutant form of the polypeptide. When a cell proliferative disorder is associated with 5'ALT or 5'ALT-p16 or -p15 overexpression, such suppressive reagents as antisense polynucleotide sequence or 5'ALT or 5'ALT-p16 or -p15 binding antibody can be introduced to a cell. In addition, polynucleotides encoding p16 or p15 can be introduced into the cell to regulate cell proliferation. Alternatively, when a cell proliferative disorder is associated with underexpression or no expression, or expression of a mutant 5'ALT or 5'ALT-p16 or -p15 polypeptide, a sense polynucleotide sequence (the DNA coding strand) or 5'ALT or 5'ALT-p16 or -p15 polypeptide can be introduced into the cell.

The invention provides a method for detecting a cell expressing 5'ALT or 5'ALT-p16 or -p15 or a cell proliferative disorder associated with 5'ALT or 5'ALT-p16 or -p15 comprising contacting a cell suspected of expressing 5'ALT or 5'ALT-p16 or -p15 or having a 5'ALT or 5'ALT-p16 or -p15 associated disorder, with a reagent which binds to the component. The cell component can be nucleic acid, such as DNA or RNA, or protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation. Such analyses include detection analysis for loss of a region of 9p21.

The 5'ALT or 5'ALT-p16 or -p15 polynucleotide that is an antisense molecule is useful in treating malignancies of the various organ systems, particularly, for example, cells in the central nervous system, including neural, lung, ovary, uterus, breast, head and neck, liver, pancreas tissue, etc. Essentially, any disorder which is etiologically linked to altered expression of 5'ALT or 5'ALT-p16 or -p15 or expression of an altered gene product could be considered susceptible to treatment with a 5'ALT or 5'ALT-p16 or -p15 modulating reagent. One such disorder is a malignant cell proliferative disorder, for example.

For purposes of the invention, an antibody or nucleic acid probe specific for 5'ALT or 5'ALT-p16 or -p15 may be used to detect and/or to bind to 5'ALT or 5'ALT-p16 or -p15 polypeptide (using antibody) or polynucleotide (using nucleic acid probe) in biological fluids or tissues. Any sample containing a detectable amount of 5'ALT or 5'ALT-p16 or -p15 can be used. A sample can be a liquid such as urine, saliva, cerebrospinal fluid, blood, serum and the like, a cytological sample, a tumor, or sample thereof, or a solid or semi-solid such as tissues, feces, and the like, or, alternatively, a solid tissue such as those commonly used in histological diagnosis.

The invention provides a method for detecting a cell proliferative disorder which comprises contacting an anti-5'ALT or 5'ALT-p16 or -p15 antibody or nucleic acid probe with a cell suspected of having a 5'ALT or 5'ALT-p16 or -p15 associated disorder and detecting binding to the antibody or nucleic acid probe. The antibody reactive with 5'ALT or 5'ALT-p16 or -p15 or the nucleic acid probe is preferably labeled with a compound which allows detection and quantitation of binding to 5'ALT or 5'ALT-p16 or -p15. Any specimen containing a detectable amount of antigen or polynucleotide can be used. The level of 5'ALT or 5'ALT-p16 or -p15 in the suspect cell can be compared with the level in a normal cell or the nature of the transcript or gene product can be compared with a normal cell, in order to determine whether the subject has a 5'ALT or 5'ALT-p16 or -p15-associated cell proliferative disorder. Preferably the subject is human.

When the cell component is nucleic acid, it may be necessary to amplify the nucleic acid prior to binding with an 5'ALT or 5'ALT-p16 or -p15 specific probe. Preferably, polymerase chain reaction (PCR) is used, however, other nucleic acid amplification procedures such as ligase chain reaction (LCR), ligated activated transcription (LAT), QB replicase, and nucleic acid sequence-based amplification (NASBA) may be used.

The present invention identifies a nucleotide sequence that can be expressed in an altered manner as compared to expression in a normal cell, therefore it is possible to design appropriate therapeutic or diagnostic techniques directed to this sequence.

Detection of elevated levels of 5'ALT or 5'ALT-p16 or -p15 expression is accomplished by hybridization of nucleic acids isolated from a cell suspected of having an 5'ALT or 5'ALT-p16 or -p15 associated proliferative disorder with an 5'ALT or 5'ALT-p16 or -p15 polynucleotide of the invention. Techniques commonly used in the art, for example, Northern Blot analysis, PCR, or RNase protection assays, are utilized to quantitate expression of 5'ALT or 5'ALT-p16 or -p15. Other standard nucleic acid detection techniques will be known to those of skill in the art.

Treatment of an 5'ALT or 5'ALT-p16 or -p15 associated cell proliferative disorder includes modulation of 5'ALT or 5'ALT-p16 or -p15 gene expression and 5'ALT or 5'ALT-p16 or -p15 activity. The term "modulate" envisions the suppression of expression of 5'ALT or 5'ALT-p16 or -p15 when it is over-expressed, or augmentation of 5'ALT or 5'ALT-p16 or -p15 expression when it is under-expressed. When a cell-proliferative disorder is associated with the expression of 5'ALT or 5'ALT-p16 or -p15, agents which induce reexpression of p15 or p16 or nucleic acid sequences that interfere with 5'ALT or 5'ALT-p16 or -p15 expression at the translational level can be used. For example, when the disorder is associated with 5'ALT expression or increased methylation resulting in decreased transcription, such methylation suppressive agents as 5-azacytidine can be introduced into a cell. Other similar agents will be known to those of skill in the art. The nucleic acid approach utilizes, for example, antisense nucleic acid, ribozymes, or triplex agents to block transcription or translation of a specific 5'ALT or 5'ALT-p16 or -p15 mRNA, either by masking that mRNA with an antisense nucleic acid or triplex agent, or by cleaving it with a ribozyme. Such disorders include neurodegenerative diseases, for example.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target 5'ALT or 5'ALT-p16 or -p15-producing cell. The use of antisense methods to inhibit the in vitro translation of genes is well known in the art (Marcus-Sakura, *Anal.Biochem.*, 172:289, 1988).

Use of since the oligtide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasseihoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Treatment of an 5'ALT or 5'ALT-p16 or -p15 associated cell proliferative disorder also includes modulation of 5'ALT or 5'ALT-p16 or -p15 gene expression and 5'ALT or 5'ALT-p16 or -p15 activity by increasing or decreasing the activity or expression from the GT-rich promoter region of 5'ALT. For example, antisense or other nucleic agents are useful for blocking the promoter region, thereby inhibiting expression. Those of skill in the art will know other agents which are useful for increasing or decreasing expression from a promoter region.

The present invention also provides gene therapy for the treatment of cell proliferative or immunologic disorders which are mediated by 5'ALT or 5'ALT-p16 or -p15 protein. Such therapy would achieve its therapeutic effect by introduction of the 5'ALT or 5'ALT-p16 or -p15 antisense polynucleotide into cells having the proliferative disorder. Alternatively, it may be desirable to introduce polynucleotides encoding full length p16 or p15 into cells. Delivery of antisense 5'ALT or 5'ALT-p16 or -p15 polynucleotide or p16 or p15 polynucleotide, can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a 5'ALT or 5'ALT-p16 or -p15 sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the 5'ALT or 5'ALT-p16 or -p15 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Ψ2, PA317 and PA 12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for 5'ALT or 5'ALT-p16 or -p15 antisense polynucleotides or p16 or p15 polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unicellular vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies or polynucleotides of the invention can be used in vitro and in vivo to monitor the course of amelioration of a 5'ALT or 5'ALT-p16 or -p15-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the 5'ALT or 5'ALT-p16 or -p15-associated disease is effective. The term "ameliorate" denotes a lessening of the detrimental effect of the 5'ALT or 5'ALT-p16 or -p15-associated disease in the subject receiving therapy.

The identification of a novel member of the cell cyclin regulatory genes provides a useful tool for diagnosis, prognosis and therapeutic strategies associated with p16 and p15mediated cell proliferative disorders. Measurement of polypeptide levels using antibodies is a useful diagnostic for following the progression or recovery from cellular proliferative diseases including cancer.

As discussed in the background section above, the gene encoding the tumor suppressor p16 and regions on chromosome 9p21 have been found to be deleted in certain cancers, thus allowing unchecked cellular proliferation to occur. Logically, if a gene encoding a tumor suppressor or a regulator of a tumor suppressor contains a polymorphism that compromises the activity of the suppressor, then tumors may develop over time even without deletion of the gene encoding the suppressor. In the particular case of the 5'ALT gene, its presence on chromosome 9p21 suggests that both deletions and polymorphisms of the gene may contribute to the onset of certain familial and environmental cancers. Therefore, the invention also provides a method of detecting the presence or absence of all or particular regions of human chromosome 9p21, comprising contacting a sample containing human chromosomal DNA with a polynucleotide of SEQ ID NO:1, and detecting the hybridization of the chromosomal DNA with the polynucleotide of SEQ ID NO:1.

More specifically, the role of 5'ALT in forming alternate transcripts and truncated p16 and p15 polypeptides indicates that an excessive level of kinases can be expected to develop within cells that harbor 5'ALT gene deletions or polymorphisms that compromise the ability of p16 to inhibit CDK4, for example. Thus, while deletions of the 5'ALT gene may be indicative of a pre-malignancy or malignancy, polymorphisms in the gene (particularly polymorphisms in germline cells of persons with a familial history of 9p21-linked cancers) may be indicative of a susceptibility to develop a "cancer condition" (i.e., a condition which is causatively related to excessive cellular levels of CDK4).

In its broadest sense, the present invention allows the detection of any polymorphism in, or deletion of, a 5'ALT target nucleic acid sequence of diagnostic or therapeutic relevance, where the target nucleic acid sequence is present in a biological cell sample such as that heretofore subjected to histopathologic examination using techniques of light microscopy, such as the margins of a primary tumor or a regional lymph node. Thus, the target nucleotide sequence may be, for example, a mutant nucleotide, a restriction fragment length polymorphism (RFLP), a nucleotide deletion, a nucleotide substitution, or any other mammalian nucleic acid sequence of interest in such tissue specimens. As used herein the term "polymorphism" as applied to a target 5'ALT nucleotide sequence shall be understood to encompass a mutation, a restriction fragment length polymorphism, a nucleic acid deletion, or a nucleic acid substitution.

In the case of deletions and polymorphisms, this information can be used to diagnose a pre-cancerous condition or existing cancer condition. Further, by quantitating the number of cells in successive cell samples which bear and acquire the deletion or polymorphism at separate locations in the body and/or over time, the progression of a cancer condition can be monitored. Similarly, where a deletion or polymorphism is found in a patient who has not yet developed symptoms of a cancer condition (particularly one who carries the abnormality in germline cells and/or has a family history of a particular cancer condition), the deletion or polymorphism will be indicative of a genetic susceptibility to develop the cancer condition. Such susceptibility can further be evaluated on a qualitative basis based on information concerning the prevalence, if any, of the cancer condition in the patient's family history and the presence of other risk factors, such as exposure to environmental factors and whether the patient also carries cells having a deletion of the gene for cell cyclin inhibitors or regulators.

In order to detect the alteration of the wild-type 5'ALT gene in a tissue sample, means known in the art are used to enrich for tumor cells. Detection of point mutations may be accomplished by molecular cloning of the allele(s) presenting the tumor tissue and sequencing the allele(s) using techniques known in the art. Alternatively, the polymerase chain reaction can be used to amplify gene sequences directly from genomic DNA preparations from the tissue (see EXAMPLES). Specific primers which can be used in order to amplify the gene will be discussed in detail in the EXAMPLES. Because 5'ALT resides in close proximity to the p15 and p16 loci on chromosome 9p21, 5'ALT specific primers can also be utilized for amplification and detection of polymorphisms, deletions, point mutations, etc., in the p 15 or p 16 gene, as well.

The following examples are intended to illustrate but not limit the invention. While they are typical of those that might be used, other procedures known to those skilled in the art may alternatively be used.

EXAMPLES

The finding that de novo methylation of a 5' CpG island led to transcriptional block of full length p16 in many neoplasms, led to the present finding of the presence of an alternative promoter or initiation site for p15 and p16. The present EXAMPLES show the identification of an abundant p16 and p15 alternative transcript generated from a novel 5'ALT sequence, involved in the complex regulation of these cell cycle related genes.

Example 1

Materials and Methods
1. Cell lines and primary tumors

Cell lines used in this study included those derived from primary head and neck squamous cell carcinomas at Hopkins (003, 006, 011, 012, 020, 022, 029, 030) or elsewhere (A439, A549, UMSCC), Hela, and a normal lymphoblastoid line L89. Primary tumors included 14 non-small cell lung cancers, 8 small cell lung cancers, 15 pancreatic adenocarcinomas and 13 head and neck squamous cell carcinoma collected at the Johns Hopkins Hospital (diagnosis was confirmed by pathology). Tumors were microdissected to remove non-neoplastic cells and genomic DNA or total RNA were extracted as described previously (Mao, L., et al., *Cancer Res.*, 54:1634–1637, 1994; Chomczynski, P. and Sacchi, N., *Analyt. Biochem.*, 162:156–159, 1987).

2. "Inverse" PCR

A specific antisense primer from the 3' untranslated region of p16 (5'-TCCCGAGGTTTCTCAGAG-3') (SEQ ID NO:2) was used for reverse transcription of total RNA (5 μg each from tumor or normal lymphoblastoid cell lines) by using 200 U Superscript II RNase HRT in the presence of dNTPs and double stranded cDNA was then synthesized following the manufacturer's protocol (GibcoBRL, Gaithersburg, USA). Self-ligation of the blunt end cDNAs was performed in 100 ul reaction volume containing 50U T4 DNA ligase (GibcoBRL) as previously described (Zeiner, M. And Gehrig, U., *Biotechniques,* 17:1051–1053, 1994) 5 µl of each ligation product was used for PCR amplification as described (Sidransky, et al., *Science,* 252: 706–709, 1991) by utilizing primers in exon 2 of p16; the sense 5'-CAUCAUCAUCAUGATGTCGCACGGTACCTG-3' (SEQ ID NO:3) and antisense 5'-CUACUACUACUAACGGGTCGGGTGAGAGTG-3' (SEQ ID NO:4) primers were oriented away from each other. The PCR products were then cloned into a plasmid vector (pBSK, Strategene). At least 10 clones were sequenced for each sample by direct sequencing following the manufacture's protocol (Perkin Elmer) (see below).

3. RT-PCR

2 µg total RNA was subjected to reverse transcription with random hexamers, dNTPs, and 200 U Superscript II RNase H RT (GibcoBRL) in a 20 µl reaction volume as above. PCR amplification was performed by using primers P1 (5'-AGTGGCGCTGCTCACCTC-3') (SEQ ID NO:5) and P2 (5'-TCCCGAGGTTTCTCAGAG-3') (SEQ ID NO:6) for the p16ALT cDNA fragment, and P1 and P3 (5'-GGGTGGGAAATTGGGTAAG-3') (SEQ ID NO:7) for the p15ALT cDNA fragment. The products were run on 1% agarose gel and visualized by ethidium bromide staining.

In the methylation studies, the cDNA was then amplified by PCR using the forward primer for exon 1 and the reverse primer for exons 2 or 3 of CDKN2/p16 yielding a 428 or 477 kb fragment respectively, which was run on 1.5% agarose gel. As a control, the 321 kb fragment of p53 was amplified simultaneously. All reactions were repeated at least once.

4. RNAase protection assay 485 bp of a p16 cDNA fragment (including exon 1, 2, 3 and partial 3' UTR) was cloned into the pBSK vector (Strategene). An antisense p16 RNA probe containing γ-[$^{32}$P-UTP] was then synthesized by using a invitro transcription kit and isolated by gel electrophoresis (Ambion). 100 µg of total RNA from each sample was co-precipitated with labelled probe and hybridized overnight at 45° C. After NRase treatment of hybridized products, samples were concentrated by ethanol precipitation, separated on 5% acrylamide/8M urea gel, and exposed to film.

5. Primer extension assay

An antisense primer of 5'ALT (5'-GGGTCACCAAGAACCTGC-3' (SEQ ID NO:8) was end labelled with γ-[$^{32}$P-ATP] and T4 DNA polynucleotide Kinase (New England). 100 µg total RNA was used for each reaction. After co-precipitation of the primer and RNA, samples were incubated in the hybridization buffer at 30° C. for overnight. Reverse transcription was performed at 42° C. for 60 minutes with 200 U of Superscript II RNase H RT in the presence of dNTPs (GibcoBRL). After treatment with RNase H, samples were concentrated by ethanol precipitation and separated on 6% acrylamide/8M urea gel. A standard sequence of the p53 gene was used as a size marker after exposing to film.

6. Restriction mapping

Exon 1 of p16 was labeled by random priming and used to probe the chromosome 9 cosmid library LL-9 (constructed at the Biomedical Sciences Division, Lawrence Livermore National Laboratory, Calif. 94550, sponsored by the U.S. Department of Energy.) The cosmids (217C4, 191G6, 190G8, 190D10, and 9C1) were cut with restriction enzymes EcoRI, PstI, and HinfI, run on a 0.8% agarose gel and transferred to nylon membrane. Exons 1 and 2 of both p16 and p15 and 5'ALT were labelled by random priming and hybridized to the blots.

7. Sequence analysis

Primary tumor or cell line DNA was amplified by PCR with primers 5'-TCCCAGTCTGCAGTTAAGG-3' (SEQ ID NO:9) and 5'-GTCTAAGTCGTTGTAACCCG-3' (SEQ ID NO:10) as described (Sidransky, 1991, supra). 10–50 ng of amplified DNA was utilized for each sequence reaction. Sequencing primers 5'-AGTGCATCAGCACGAGGG-3' (SEQ ID NO:11) and 5'-AACATGGTGCGCAGGTTC-3' (SEQ ID NO:12) were labelled by γ-$^{32}$P-[ATP] at the 5' end and subjected to PCR amplification for 25 cycles using the AmpliCycle™ sequencing kit (Perkin Elmer) according to manufacturer's protocol. 2.5 µl of each amplified product was run on 6% acrylamide/8M urea gel and exposed to film.

8. TNT Assay

2 µg of total RNA was used for reverse transcription as described above in the presence of hexamers and dNTPs. PCR amplification was performed as described previously using primers TNT-P16 (Jen, et al., *Cancer Res.,* 54:6353–6358, 1994) and P2 for p16 cDNA; P4 (5'-GG-ATCCTAATACGACTCACTATAGGGAGACCACCATG-GCGCTGCTCACCTCTGGTG-3') (SEQ ID NO:13) and P2 for p16ALT cDNA in 25 µl reaction volume. After phenol-chloroform extraction and ethanol precipitation, ¹⁄₁₀ of the products from each sample was subjected to a TNT in vitro transcription and translation assay reaction in 10 µl volume by using a commercial TNT kit (Promega). 2 µl of in vitro translated product was run on a 15% SDS-PAGE gel enhanced with Amplify® (Amersham) and exposed to film.

9. Immunoprecipitation

2 µl of in vitro translated product was incubated with either N-terminal or C-terminal polyclonal antibodies to p16 (Santa Cruz Biotechnology) in RIPA (10 mM Tris, pH7.5, 1% Na deoxycholate, 1% NP40, 150 mm NaCl and 0.1% SDS) at 4° C. overnight and then shaken with Sepharose A beads for 60 minutes. After washing three times with RIPA buffer, the products were run on 15% SDS-PAGE gels and exposed to films.

Example 2

Identification of 5'Alt

To identify the transcriptional start site of p16, a specific antisense primer (from the 3' untranslated region) was used for reverse transcription of total RNA from a normal lymphoblastoid cell line. Following reverse transcription, double stranded cDNA synthesis ligation was performed in large volume (Zeiner, 1994, supra). The resulting circular product was amplified by PCR (so called "inverse" or "bubble" PCR) utilizing primers in exon 2 of p16 oriented away from each other and then cloned into a plasmid vector. Ten individual clones were then sequenced completely. Although clones with the previously described exon 1 of p16 were identified, most clones (6 of 10) contained a novel 5' sequence spliced precisely onto (the first base of) exon 2 of p16. This novel 268 bp fragment (named 5'ALT for alternative) contained a theoretical open reading frame (ORF) but was not in frame with the putative coding sequence of exons 2 and 3 of p16 (FIG. 1*a*).

Thus, the originally described exon 1 of p16 was completely excluded from this alternative transcript.

Figure 2A:
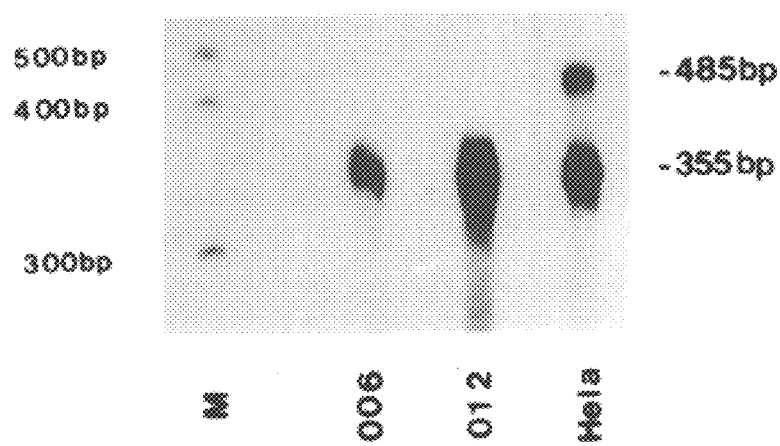
FIG. 2a shows an RNase protection assay used with a 485 bp $p16^{INK4A}$ cDNA fragment (including exon 1, 2, 3 and partial 3'UTR) as the probe. 006 and 012 designate head and neck squemous cell carcinoma cell lines in which methylation of the 5'CpG island of $p16^{INK4A}$is associated with absence of full length $p16^{INK4A}$ mRNA (485 bp). Hela cell line contains normal $p16^{INKA}$ mRNA and all cell lines contain a more abundant 355 bp smaller fragment.
Figure 2B:
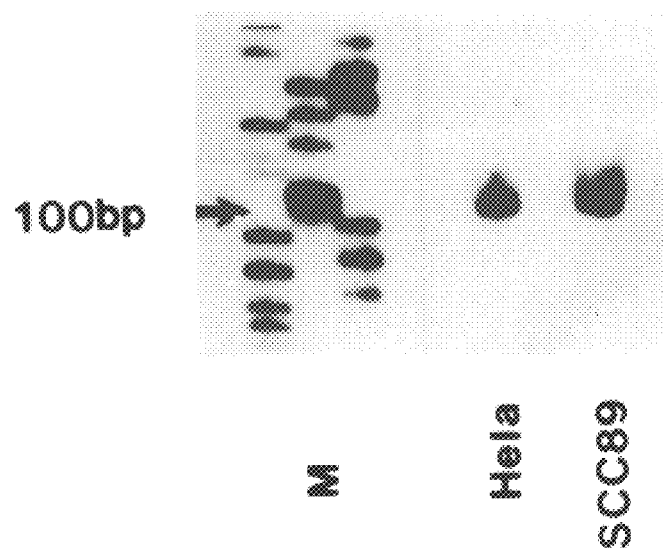
FIG. 2b shows a primer extension assay showing the expected initiation site of transcription for 5'ALT (100 bp from the primer) in both a Hela cell line and normal lymphoblastoid cell line (L89).

RNAase protection with a full length p16 probe demonstrated the presence of the originally described full length p16 product (FIG. 2*a*). However, the smaller and more abundant product results from cleavage of the 5'ALT sequence with protection of the shared p16 portion that contains exons 2 and 3. This predominant transcription initiation site was also confirmed by direct primer extension of total RNA (FIG. 2*b*).

Example 3

Genomic Localization of 5'ALT

Genomic localization of the 5'ALT sequence was performed by using a specific oligomer derived from 5'ALT to probe a chromosome 9 cosmid library. One of the hybridizing cosmid clones contained both p16 and p15. EcoR1 restriction mapping of this cosmid and other hybridizing clones yielded a small contig (approx 80 kb) of the region. Successive Southern blot hybridization with all exons of p16 and p 15 (and the 5'ALT ORF) to the cosmid contig was performed. 5'ALT was found to be on the same 8.5 kb fragment with exon 2 of p15 and two cosmids contained 5'ALT but not exon 1 from p15. These findings and those below are compatible with localization of 5'ALT upstream to exon 2 of p15 (FIG. 1b).

One of the cosmids was then used to derive the complete surrounding genomic sequence of 5'ALT (FIG. 1a) which is notable in several respects. First, the region is CpG rich and there is a GT rich region upstream of 5'ALT suggestive of a GT box promoter element. Second, a consensus Kozak element is contained at an AUG site at position 75 (nucleotide). Additionally, a long microsatellite ($CA_n$) repeat sequence is located downstream and has been confirmed to be highly polymorphic.

The localization of 5'ALT upstream to exon 2 of p15 (and extensive conservation of the 5' intron/exon boundary of exon 2 in both p16 and p15) led to the investigation of the presence of a 5'ALT p15 product. As for 5'ALT-p15, "inverse" PCR was performed with a p15 specific primer and a similar 5'ALT product was obtained which was spliced to exon 2 of p15. RT PCR of total RNA from eight tumor cell lines (without homozygous deletion of this region) confirmed the presence of both alternative transcripts (p15ALT and p16ALT) in all cases. Sequence analysis of 5'ALT sequences in these eight tumor cell lines and in several primary tumors with hemizygous loss of 9p21 has not yet revealed a point mutation.

Example 4

Transcription and Translation from 5'ALT

Figure 2C:
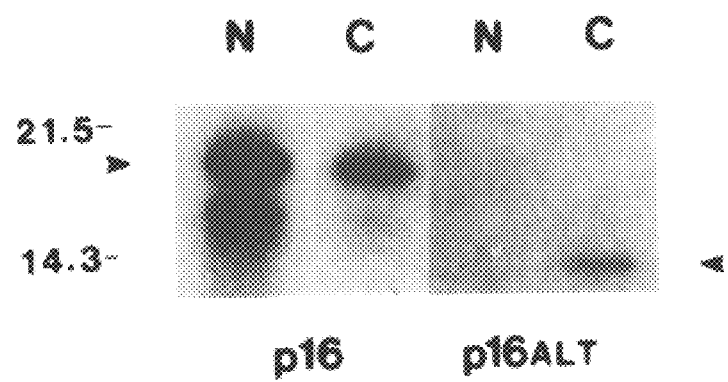
FIG. 2c shows immunoprecipitation of in vitro translated p16 and 5'ALT-p16 with a C-terminal antibody to p16(C), or an antibody to only the N-terminal portion of p16 (N). p16-5'ALT is recognized by the C-terminal antibody but not by the N-terminal antibody, whereas p16 is recognized by both antibodies.

Complete p16 and p16-5'ALT cDNA was amplified by RT-PCR and subjected to labelled in vitro transcription and translation (TNT). As shown in FIG. 2c, the smaller p16-5'ALT product migrated at approximately 9–10 kD on SDS/PAGE gels. To see if this product was translated in frame from the third Met of p16 (just inside exon 2 and consensus Kozak sequence), immunoprecipitation was performed using polyclonal anti-p16 antibodies that recognize either the C-terminus or the N-terminus. As expected, the TNT p16ALT product was recognized by the C-terminal but not the N-terminal antibody providing strong evidence that this product lacked the N-terminal exon 1 coding sequence.

Example 5

Cell Lines Methylated at the 5' CpG Island CDKN2/p16 Show Lack Of Transcription 5' CpG island methylation is usually associated with loss of transcription. Therefore, RNA derived from 23 cell lines was subjected to reverse transcriptase (RT)-PCR using primers amplifying a 428 bp cDNA stretch corresponding to the first and second exon of CDKN2/p16. Strinkingly, none of the methylated cell lines (6 NSCLC, 1 SCLC, 3 HNSCC) expressed CDKN2/p16, while a control RT-PCR product of exons 3 and 4 of p53 was readily detectable. In contrast, all the unmethylated cell lines (2 NSCLC, 6 SCLC, 4 HNSCC) expressed this 428 bp product of CDKN2/p16. As for other genes on the X-chromosome or in imprinted regions, it is methylation at the 5' CpG island that consistently and reproducably correlated with the transcriptional block of CDKN2/p16.

Interestingly, primers designed to amplify exons 2 and 3 of the CDKN2/p16 cDNA, yielded the appropriate size product of 352 bp in all cell lines regardless of 5' CpG island methylation status. Further analysis disclosed a novel cDNA product that consists of a distinct 5' UTR spliced to exons 2 and 3 of CDKN2/p16 cDNA. This product, excluding exon 1 of CDKN2/p16, initiates transcription at a locus upstream of CDKN2/p16.

Summary

The presence of other AUG sites and a long UTR in 5'ALT favors diminished translation of the 5'ALT transcripts (Kozak, M., *Ann. Rev. Cell Biol.*, 8:197–225, 1992). The TNT studies presented herein much weaker translation efficacy for p16ALT in comparison to p16 (FIG. 2c). Other Cylcin/CDK inhibitors are known to undergo extensive transcriptional regulation and in the case of $p27^{KiP1}$, unusual post-transcriptional regulation (Hunter, T. and Pines, J., *Cell*, 79:573–582, 1994). Thus this 5'ALT sequence most likely represents an untranslated ORF that plays a role in the complex regulation of these cell cycle inhibitors. The presence of abundant alternative transcripts for p16 and p15 may provide an explanation for certain issues regarding their role as tumor suppressor genes. The absence of p15 and p16 point mutations in many primary tumors may reflect their complex genomic organization and regulation in the 9p21 region, perhaps resulting in strong selection for alternative mechanisms of inactivation in human cancers.

Although the invention has been described with reference to the presently preferred embodiment, it should be understood that various modifications can be made without departing from the spirit of the invention. Accordingly, the invention is limited only by the following claims.

---

I claim:

1. A substantially pure polypeptide encoded by a polynucleotide as set forth in SEQ ID NO:1.

2. A substantially pure polypeptide encoded by a polynucleotide as set forth in SEQ ID NO:1 and further comprising exon 2 and 3 of p16 cyclin CDK inhibitor.

3. A substantially pure polypeptide encoded by a polynucleotide as set forth in SEQ ID NO:1 and further comprising exon 2 of p15 cyclin CDK inhibitor.

* * * * *